United States Patent
Wyvratt et al.

(10) Patent No.: US 7,504,501 B2
(45) Date of Patent: Mar. 17, 2009

(54) ANTIPROTOZOAL IMIDAZOPYRIDINE COMPOUNDS

(75) Inventors: Matthew J. Wyvratt, Mountainside, NJ (US); Tesfaye Biftu, Westfield, NJ (US); Michael H. Fisher, Ringoes, NJ (US); Dennis M. Schmatz, Cranford, NJ (US)

(73) Assignee: Merial Limited, Duluth, GA (US)

( * ) Notice: Subject to any disclaimer, the term of this patent is extended or adjusted under 35 U.S.C. 154(b) by 386 days.

(21) Appl. No.: 10/548,154

(22) PCT Filed: Mar. 2, 2004

(86) PCT No.: PCT/US2004/006153

§ 371 (c)(1),
(2), (4) Date: Sep. 6, 2005

(87) PCT Pub. No.: WO2004/080390

PCT Pub. Date: Sep. 23, 2004

(65) Prior Publication Data

US 2006/0178358 A1 Aug. 10, 2006

Related U.S. Application Data

(60) Provisional application No. 60/452,467, filed on Mar. 6, 2003.

(51) Int. Cl.
C07D 403/04 (2006.01)
A61K 31/429 (2006.01)

(52) U.S. Cl. .................. 544/180; 544/182; 544/238; 544/333; 546/121; 514/241; 514/242; 514/252.04; 514/256; 514/300

(58) Field of Classification Search ............. 544/180, 544/182, 238, 333; 546/121; 514/241, 242, 514/252.04, 256, 300
See application file for complete search history.

(56) References Cited

FOREIGN PATENT DOCUMENTS

WO    WO 03/000682 A1    1/2003

*Primary Examiner*—Deepak Rao
(74) *Attorney, Agent, or Firm*—Judy Jarecki-Black; Merial Limited; Thomas Kowalski, Esq.

(57) ABSTRACT

Compounds described by the Formula (I): (I) or pharmaceutically acceptable salts, or N-oxides thereof. The compounds are useful for the treatment and prevention of protozoal diseases in mammals and birds. A method for controlling coccidiosis in poultry comprises administering an effective amount of the compound alone, or in combination with one or more anticoccidial agent(s). A composition for controlling coccidiosis in poultry comprises the compound alone, or in combination with one or more anticoccidial agent(s). Methods for the treatment and prevention of mammalian protozoal diseases, such as, for example, toxoplasmosis, malaria, African trypanosomiasis, Chagas disease, and opportunistic infections comprise administering the compound alone, or in combination with one or more antiprotozoal agent(s).

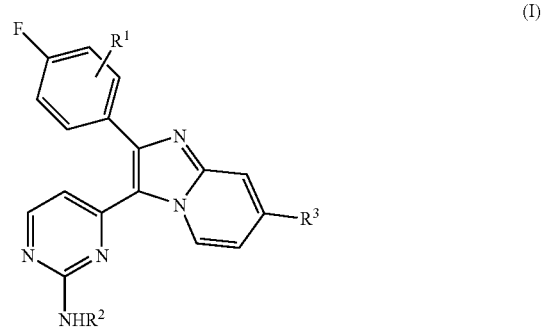

(I)

15 Claims, No Drawings

ANTIPROTOZOAL IMIDAZOPYRIDINE COMPOUNDS

RELATED APPLICATION DATA

This is a National filing under 35 USC 371 of PCT/US2004/006153, filed Mar. 2, 2004, which claims priority from USSN 60/452,467, filed Mar. 6, 2003.

FIELD OF THE INVENTION

The present invention relates to imidazopyridines useful for the treatment and prevention of protozoal diseases in mammals and birds. In particular, this invention relates to trisubstituted imidazopyridines that are useful for the treatment and prevention of coccidiosis in poultry. The compounds of the instant invention are also useful for the treatment and prevention of mammalian protozoal diseases, including toxoplasmosis, malaria, African trypanosomiasis, Chagas disease and opportunistic infections.

BACKGROUND OF THE INVENTION

Parasitic protozoa are responsible for a wide variety of infections in both humans and animals. Protozoans of the genus *Eimeria* cause coccidiosis, a widespread disease of domesticated animals that causes severe pathology in the intestines and ceca. The most pathological species in this genus include *E. tenella, E. acervulina, E. mitis, E. necatrix, E. brunetti* and *E. maxima*. Animal coccidiosis is generally spread by animals picking up the infectious organism from droppings on contaminated litter or the ground, or from food or drinking water. Coccidiosis is manifested by hemorrhage, accumulation of blood in the ceca, passage of blood in the droppings, weakness and digestive disturbances. The disease often terminates in the death of the animal, while those that survive severe coccidiosis infection have had their market value substantially reduced as a result of such infections. Coccidiosis is, therefore, a disease of great economic importance. Accordingly, extensive work has been done to find new and improved methods for controlling and treating coccidial infections in animals.

In the poultry industry, it is common practice to include anticoccidial agents in poultry feed for most of the bird's life to control or prevent coccidiosis outbreak. However, there is a risk that the causative organisms will develop resistance after continuous or repeated exposure to any particular anticoccidial agent. Furthermore, conventionally used anticoccidial agents such as sulfanilamides, nitrofurans, quinolines, antithiamines, benzoamides, and polyether-based antibiotics are often toxic to the hosts. Therefore, there is a continuing need to identify new anticoccidial compounds, preferably in a different chemical class from agents currently in use.

Parasitic protozoa are also responsible for a variety of human diseases, many of which are life threatening. Malaria remains a significant health threat to humans despite massive international attempts to eradicate the disease. Another parasitic disease, trypanosomiasis, poses health risks to millions of people across multiple countries in Africa, South and Central America, and Mexico. Visitors to these regions, such as business travelers and tourists, are also at risk for contracting parasitic diseases. There are two types of African trypanosomiasis, also known as sleeping sickness. One type is caused by the parasite *Trypanosoma brucei gambiense*, and the other is caused by the parasite *Trypanosoma brucei rhodesiense*. If left untreated, African sleeping sickness results in death. Chagas disease, caused by *Trypanosoma cruzi*, affects millions of people in South and Central America, and Mexico. Untreated Chagas disease causes decreased life expectancy and can also result in death. There is currently no drug available for the prevention of these diseases. Currently available treatments are not entirely effective, and can even be toxic to the patient. A need thus exists for an antiparasitic compound for humans that is more effective and less toxic than those currently available.

The risk of parasitic diseases is also present outside developing countries. Opportunistic infections in immunocompromised hosts caused by *Pneumocystis carinii, Toxoplasma gondii*, and *Cryptosporidium* sp. are becoming increasingly prevalent in developed countries. For example, toxoplasmosis, which is caused by the parasite *Toxoplasma gondii*, is found in countries throughout the world, including the United States. Pregnant women and those with weak immune systems are particularly susceptible to health risks resulting from *Toxoplasma* infection. Severe toxoplasmosis can result in damage to the brain, eyes, and other organs. Currently available treatments for toxoplasmosis, which are the drugs trisulfa-pyrimdine, sulfadiazine and pyrimethamine, are not effective, and can be toxic to the host. Therefore, there is a need for therapeutic agents to treat toxoplasmosis that are more effective and less toxic than currently available treatment agents.

PCT Published Application WO03/000682 discloses compounds of the formula:

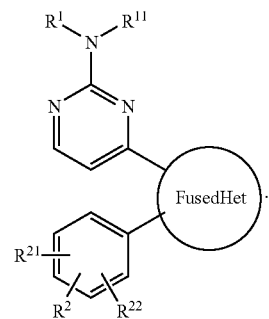

PCT Published Application WO03/000689 discloses compounds of the formula:

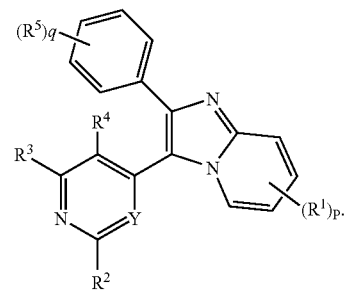

SUMMARY OF THE INVENTION

The present invention is directed to trisubstituted imidazopyridines that are useful for the treatment and prevention of protozoal diseases in mammals and birds. The present invention is also directed to compositions comprising such compounds, either alone or in combination with one or more antiprotozoal agents. The present invention further provides methods of using the instant compounds, either alone, or together with one or more anticoccidial agents, to prevent and treat coccidiosis in poultry. The compounds of the present invention are also useful for the prevention and treatment of protozoal diseases in mammals, including toxoplasmosis, malaria, African trypanosomiasis, Chagas disease, and opportunistic infections.

DETAILED DESCRIPTION OF THE INVENTION

The present invention provides compounds of Formula (I) or pharmaceutically acceptable salts, or N-oxides, thereof:

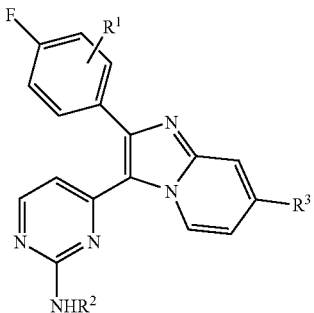

(I)

wherein $R^1$ is hydrogen, methyl or fluoro;
$R^2$ is hydrogen or methyl;
$R^3$ is selected from -L-$NR^cR^d$,

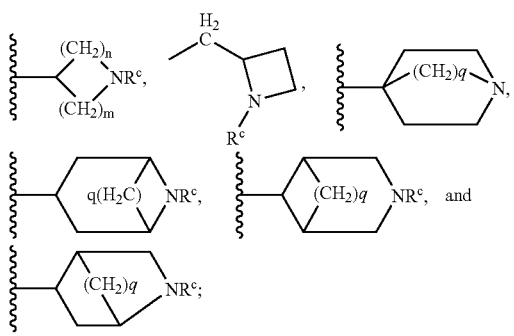

L is selected from —$(CR^aR^b)_{2-5}$— and

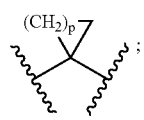

;

$R^a$ and $R^b$ are independently selected from hydrogen, OH, F, and $C_{1-4}$alkyl, provided that when $R^a$ is OH, the $R^b$ attached to the C is hydrogen or $C_{1-4}$alkyl;
or $R^a$ and $R^b$, together with the C to which they are attached, form a $C_{3-6}$cycloalkyl;
$R^c$ and $R^d$ are independently selected from hydrogen and $C_{1-4}$alkyl;
n and m are independently 0, 1, 2, 3 or 4, provided that n+m=2, 3 or 4;
q is 1 or 2; and
p is 1, 2 or 3.

In one aspect, the present invention provides a compound described by the chemical Formula (I), or a pharmaceutically acceptable salt, or an N-oxide thereof, wherein
$R^3$ is —L—$NR^cR^d$.

In a second aspect, the present invention provides a compound described by the chemical Formula (I), or a pharmaceutically acceptable salt, or an N-oxide thereof, wherein

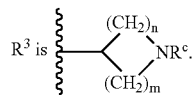

In a third aspect, the present invention provides a compound described by the chemical Formula (I), or a pharmaceutically acceptable salt, or an N-oxide thereof, wherein

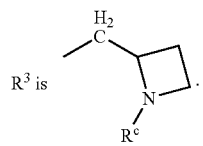

In a fourth aspect, the present invention provides a compound described by the chemical Formula (I), or a pharmaceutically acceptable salt, or an N-oxide thereof, wherein

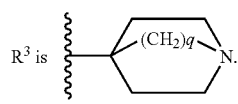

In a fifth aspect, the present invention provides a compound described by the chemical Formula (I), or a pharmaceutically acceptable salt, or an N-oxide thereof, wherein

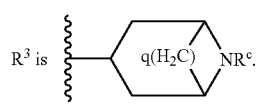

In a sixth aspect, the present invention provides a compound described by the chemical Formula (I), or a pharmaceutically acceptable salt, or an N-oxide thereof, wherein

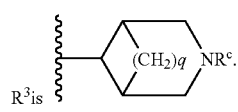

In a seventh aspect, the present invention provides a compound described by the chemical Formula (I), or a pharmaceutically acceptable salt, or an N-oxide thereof, wherein

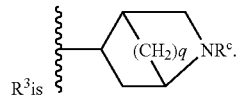

In an eighth aspect, the present invention provides a compound described by the chemical Formula (I), or a pharmaceutically acceptable salt, or an N-oxide thereof, wherein $R^3$ is piperidinyl.

In a ninth aspect, the present invention provides a compound described by the chemical Formula (I), or a pharmaceutically acceptable salt, or an N-oxide thereof, wherein $R^3$ is [N—($C_{1-4}$)alkyl]piperidinyl.

In a tenth aspect, the present invention provides a compound described by the chemical Formula (I), or a pharmaceutically acceptable salt, or an N-oxide thereof, wherein $R^3$ is piperidin-4-yl.

In an eleventh aspect, the present invention provides a compound described by the chemical Formula (I), or a pharmaceutically acceptable salt, or an N-oxide thereof, wherein $R^3$ is [N—($C_{1-4}$)alkyl]piperidin-4-yl.

In a twelfth aspect, the present invention provides a compound described by the chemical Formula (I), or a pharmaceutically acceptable salt, or an N-oxide thereof, wherein $R^3$ is [N-methyl]piperidin-4-yl.

In a thirteenth aspect, the present invention provides a compound described by the chemical Formula (I), or a pharmaceutically acceptable salt, or an N-oxide thereof, wherein $R^3$ is [N-ethyl]piperidin-4-yl.

In an fourteenth aspect, the present invention provides a compound described by the chemical Formula (I), or a pharmaceutically acceptable salt, or an N-oxide thereof, wherein $R^3$ is —$(CR^aR^b)_2$—$NR^cR^d$.

In a fifteenth aspect, the present invention provides a compound described by the chemical Formula (I), or a pharmaceutically acceptable salt, or an N-oxide thereof, wherein $R^3$ is —$CR^aR^b$—$CH_2$—$NR^cR^d$.

In a sixteenth aspect, the present invention provides a compound described by the chemical Formula (I), or a pharmaceutically acceptable salt, or an N-oxide thereof, wherein $R^3$ is —$C(OH)R^b$—$CH_2$—$NR^cR^d$.

In a seventeenth aspect, the present invention provides a compound described by the chemical Formula (I), or a pharmaceutically acceptable salt, or an N-oxide thereof, wherein L is 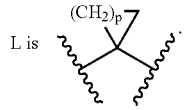.

In an eighteenth aspect, the present invention provides a compound described by the chemical Formula (D, or a pharmaceutically acceptable salt, or an N-oxide thereof, wherein L is —$(CR^aR^b)_{2-5}$—, and one $(CR^aR^b)$ represents a 1,1-($C_{3-6}$cycloalkyl).

Compounds of Formula (I) are useful in the prevention and treatment of protozoal diseases in mammals and birds. The instant compounds are useful for the prevention and treatment of mammalian protozoal diseases, including toxoplasmosis, malaria, African trypanosomiasis, Chagas disease, and opportunistic infections. The compounds are also useful for the prevention and treatment of coccidiosis in poultry.

The invention relates to compositions comprising a compound of Formula (I) alone, or in combination with one or more antiprotozoal or anticoccidial agents.

The present invention includes methods of treating and preventing coccidiosis in poultry comprising administering a prophylactically effective amount, or a therapeutically effective amount, of a compound of Formula (I) alone, or in combination with one or more anticoccidial agents.

The present invention also includes methods of treating and preventing protozoal diseases in mammals comprising administering a prophylactically effective amount, or a therapeutically effective amount, of a compound of Formula (I) alone, or in combination with one or more antiprotozoal agents.

Unless otherwise stated or indicated, the following definitions shall apply throughout the specification and claims.

The term "pharmaceutically acceptable carrier" means generally safe and tolerated by the host species being treated.

The term "prophylactically effective amount" means an amount effective to prevent a disease, illness or sickness.

The term "therapeuticlly effective amount" means an amount effective to treat, cure or ameliorate a disease, illness or sickness.

It will be understood that, as used herein, references to the compounds of the present invention are meant to also include its N-oxides and salts. The tertiary amines of the instant compounds are capable of forming N-oxides such as, for example, the following:

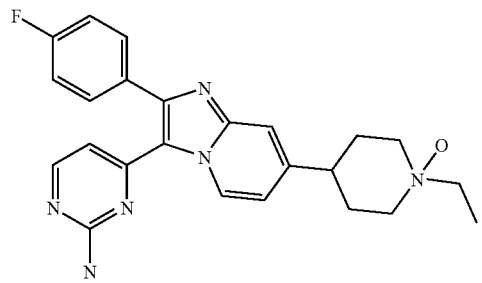

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The term "composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention, either alone, or together with one or more antiprotozoal or anticoccidial agents, and a pharmaceutically acceptable carrier.

Compositions of the present invention may be prepared in accordance with any conventional method known in the art. Thus, compositions of the present invention for controlling coccidiosis can be formulated into spreads, granules, suspensions, solutions, premixes, capsules, emulsions concentrates, tablets, feedstuff and so forth. Compositions of the present invention can contain the inventive compound either as a single substance or with or without suitable carriers that are ordinarily used for such medicaments. An excipient, such as a disintegrating agent, sliding agent, or coating agent, can be added to the instant compositions as needed in accordance with methods known in the art. The carriers usable in the instant compositions for controlling coccidiosis are not limited so long as they can be added to livestock feed or drinking water. Examples of suitable carriers include water, milk sugar, cane sugar, talc, colloidal silica, pectin, wheat flour, rice bran, corn flour, soybean, oil cake, ground or powdered grain, and other commercial livestock feeds. Although there are no specific limitations to the content or concentration of the active component, the preferable content is from about 0.1 to about 99% by weight, more preferably, from about 0.1 to about 50% by weight.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

Compounds described herein may contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The compounds of the present invention may have chiral centers other than those centers whose stereochemistry is depicted in Formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

Compounds of the present invention can be employed for the control of coccidiosis in any species. The terms "control of coccidiosis" and "controlling coccidiosis" include prophylactic use to prevent coccidiosis as well as use to treat coccidiosis after infection has occurred. Compounds of the present invention can be used for the control of coccidiosis in any poultry species, including, but not limited to, chicken, turkeys, ducks, geese, quail, pheasants, emus and ostriches. Compounds of the present invention can also be used for the control of coccidiosis in any other species, such as, for example, cattle, canines, sheep, horses, goats, and swine. Compounds of the present invention can be used to prevent or treat coccidiosis caused by any species of the causative protozoa, including *Eimeria acervulina, Eimeria brunetti, Eimeria maxima, Eimeria mitis, Eimeria necatrix, Eimeria tenella, Eimeria meleagrimitis, Eimeria gallopavonis, Eimeria adenoeides, Eimeria dispersa*.

Because coccidiosis is an intestinal malady, compounds of the present invention must be administered in a way that will allow them to reach the intestinal tract. Compounds of the instant invention can be administered according to standard methods known in the art, including by incorporating them into animal feed. The present compound can also be administered by other methods, such as by incorporating it into drinking water. In the most preferred practice, the present compound is administered in the feed.

Of the various methods of administering the compounds of this invention to poultry, the most convenient involves administering them as a component of a feed composition. The novel compound may be readily dispersed throughout feedstuff by mechanically mixing the compound in finely ground form with the poultry feedstuff, or with an intermediate formulation (premix) that is subsequently blended with other components to prepare the final poultry feedstuff. Typical components of poultry feedstuffs include molasses, fermentation residues, corn meal, ground and rolled oats, wheat shorts and middlings, alfalfa, clover and meat scraps, together with mineral supplements such as bone meal, calcium carbonate and vitamins.

When the compound according to the present invention is used as an additive to poultry feed, it is typically incorporated into a "premix." The premix contains the active agent or agents as well as pharmaceutically acceptable carriers and feedstuffs. The premix is relatively concentrated and is adapted to be diluted with other carriers, vitamin, mineral supplements, and feedstuffs to form the final animal feed. Premixes that contain an intermediate concentration of active agent, that is, a concentration between that of the first premix and the final animal feed, are sometimes employed in the industry and can be used in implementing the present invention. When employing the present compound as a sole active agent, a premix desirably contains the agent at a concentration of from about 0.1 to about 50.0% by weight. Preferred premixes will generally contain the present compound at a concentration of from about 0.5 to about 25.0%, by weight. In final feeds, the concentration of the active agent will depend on various factors known to those skilled in the art. Such factors include the relative potency of the particular active agent and the severity of the actual or potential coccidial infection. In general, a final feed employing a compound of the present invention as the sole anticoccidial will contain from about 0.002 to about 0.02% by weight of said compound, preferably from about 0.002 to about 0.01%.

The present invention contemplates using a compound of Formula (I) as the sole anticoccidial agent as well as in combination with one or more anticoccidial agents. Suitable anticoccidials for such combination use include, but are not limited to, amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril. When used in combination with one or more anticoccidial agents, the compound of Formula (I) may be administered at or lower than the effective dosage levels used for the instant compound when it is adminstered alone; for example, the final feed may contain from about 0.0001 to about 0.02% by weight, or preferably from about 0.0005 to about 0.005% of a compound of Formula (I). Similarly, the additional anticoccidial agent(s) in the combination may be used in an amount at or lower than that commonly used for the instant compound when it is administered alone. Compositions comprising a compound of Formula (I) and one or more anticoccidial agents may be formulated into medicaments for preventing or treating coccidiosis in poultry and other species as described previously.

Compositions of the instant invention can contain, in addition to anticoccidial agent(s), therapeutic or nutritional agents commonly administered to poultry in the feed or drinking water, such as, for example, parasiticides, antibacterials, and growth promoters.

The compounds of Formula I are also useful for treating parasitic diseases in mammals. These diseases include toxoplasmosis, malaria, African trypanosomiasis, Chagas disease and opportunistic infections. The terms "control of toxoplasmosis" and "controlling toxoplasmosis" include prophylactic use to prevent toxoplasmosis as well as use to treat toxoplasmosis after infection has occurred. The terms "control of malaria" and "controlling malaria" include prophylactic use to prevent malaria as well as use to treat malaria after infection has occurred. The terms "control of African trypanosomiasis" and "controlling African trypanosomiasis" include prophylactic use to prevent African trypanosomiasis as well as use to treat African trypanosomiasis after infection has occurred. The terms "control of Chagas disease" and "controlling Chagas disease" include prophylactic use to prevent Chagas disease as well as use to treat Chagas disease after infection has occurred. The terms "control of opportunistic infection" and "controlling opportunistic infection" include prophylactic use to prevent opportunistic infection(s) as well as use to treat opportunistic infection(s) after infection has occurred.

The invention includes methods of controlling toxoplasmosis, malaria, African trypanosomiasis, Chagas disease and opportunistic infections in a mammal comprising administering a compound of Formula I in an amount which is effective for controlling said disease or condition.

The dosage for the instant compounds can vary according to many factors, including the type of disease, the age and general condition of the patient, the particular compound administered, and the presence or level of toxicity or adverse effects experienced with the drug. A representative example of a suitable dosage range is from as low as about 0.025 mg to about 1000 mg. However, the dosage administered is generally left to the discretion of the physician.

The methods of treatment and prevention can be carried out by delivering the compound of Formula I parenterally. The term 'parenteral' as used herein includes intravenous, intramuscular, or intraperitoneal administration. The instant invention can also be carried out by delivering the compound of Formula I through subcutaneous, intranasal, intrarectal, transdermal or intravaginal routes.

The compounds of Formula I may also be administered by inhalation. By 'inhalation' is meant intranasal and oral inhalation administration. Appropriate dosage forms for such administration, such as an aerosol formulation or a metered dose inhaler, may be prepared by conventional techniques.

The invention also relates to a pharmaceutical composition for mammalian patients comprising a compound of Formula I and a pharmaceutically acceptable carrier. The compounds of Formula I may also be included in pharmaceutical compositions in combination with one or more other therapeutically active, or prophylactically active, compounds. For example, a composition according to the instant invention can include a combination of antiprotozoal compounds comprising a compound of Formula (I) and other antiprotozoal agent(s).

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms for mammalian patients can be employed. If a solid dosage is used for oral administration, the preparation can be in the form of a tablet, hard gelatin capsule, troche or lozenge. The amount of solid carrier will vary widely, but generally the amount of the present compound will be from about 0.025 mg to about 1 g, with the amount of solid carrier making up the difference to the desired tablet, hard gelatin capsule, troche or lozenge size. Thus, the tablet, hard gelatin capsule, troche or lozenge conveniently would have, for example, 0.025 mg, 0.05 mg, 0.1 mg, 0.5 mg, 1 mg, 5 mg, 10 mg, 25 mg, 100 mg, 250 mg, 500 mg, or 1000 mg of the present compound. The tablet, hard gelatin capsule, troche or lozenge is given conveniently once, twice or three times daily.

When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of Formula I used topically will, of course, vary with the compound chosen, the nature and severity of the condition, and can be varied in accordance with the discretion of the physician. A representative topical dose of a compound of Formula I is from as low as about 0.01 mg to as high as about 2.0 g, administered one to four times, preferably one to two times daily.

When used topically, the instant compound may comprise from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container, which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenyl-mercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol, or an oil such as castor oil or arachis oil.

Creams, ointments or pastes according to the present invention are semi-solid formulations of the active ingredient for external application. They may be made by mixing the active ingredient in finely divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

Compounds of the present invention can be evaluated by the following in vivo anticoccidiosis assay.

In Vivo Anticoccidiosis Assay:

One-day-old White Leghorn chickens are obtained from a commercial hatchery and acclimated in a holding room. At three days of age the test animals are selected by weight, wingbanded, and randomly placed on medicated or control diets for the duration of the experiment. One or two replicates of two birds are utilized per treatment. Following 24 hours premedication, in each replicate one bird is infected with *Eimeria acervulina*, the other bird is infected with *E. tenella*. Both strains of *Eimeria* are sensitive to all anticoccidial products, and have been maintained in laboratory conditions for over 25 years. The inocula consist of sporulated oocysts in tap water suspensions, administered at a dose rate of 0.25 ml per bird. The inocula levels are selected by previous dose titrations to provide a low to moderate level of infection. The *E. acervulina* portion of the experiment is terminated on Day 5, the *E. tenella* on Day 6 post infection. The measured parameters are weight gain, feed consumption and oocyst production. *E. tenella* lesion scores are also recorded for background information. Treatments which provide at least 80% reduction in oocyst production are considered active, those with 50-79% are considered partially active, and those with <50% are considered poorly active. The same numerical categories in weight gain and feed consumption differentiate among treatments with good, fair or poor productivity.

Compounds of the present invention may be prepared according to the general schemes provided below as well as the procedures provided in the Examples.

Scheme 1:

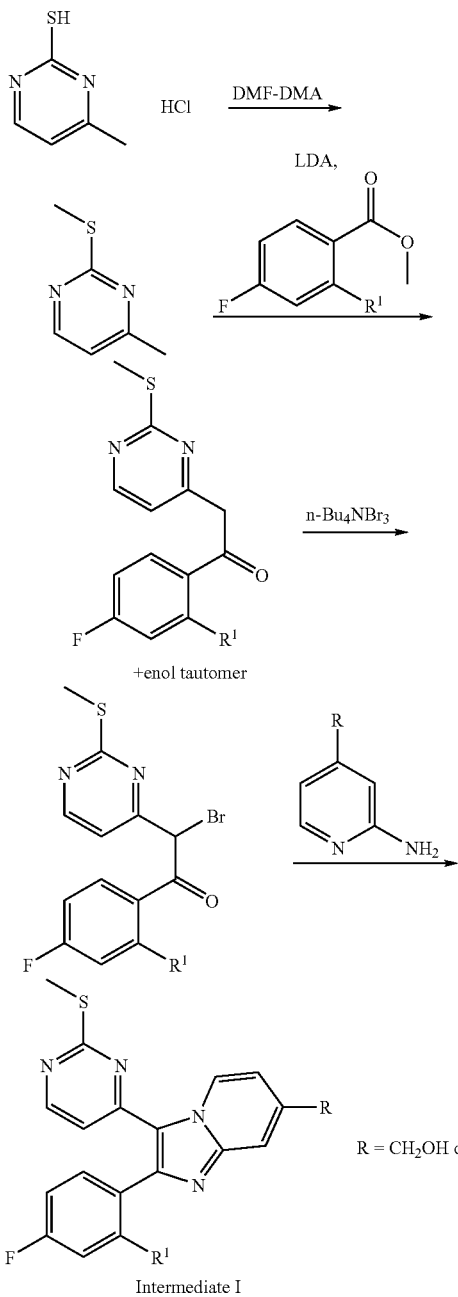

The imidazopyridine Intermediate I could be made by cyclization of bromo ketones with 2-aminopyridines such as 2-amino-4-hydorxymethylpyridine by refluxing in solvents such as ethanol. Bromo ketones could be made by brominating ketones with brominating agents such as tetra-n-butylammonium tribromide in solvents such as methylene chloride and carbon tetrachloride. The ketones used above could be made by various methods. In a typical method, the anion generated from 4-methyl pyrimidine analog and lithium diisopropylamide could be coupled with esters such as methyl 4-fluorobenzoate in solvents such as tetrahydrofuran.

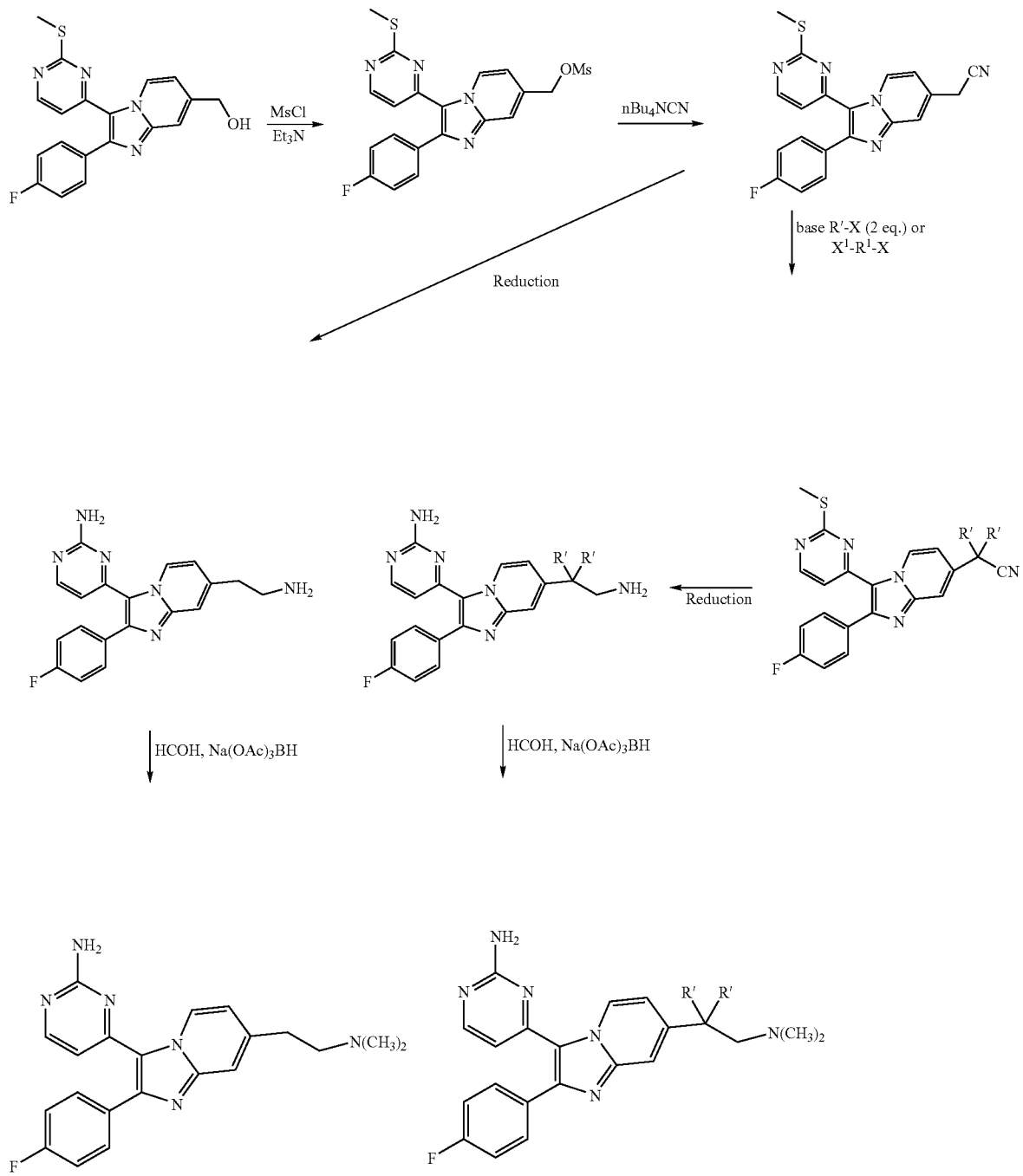

4-{7-[2-(Dimethylamino)ethyl]-2-(4-fluorophenyl)imidazo[1,2-a]-pyridin-3-yl}pyrimidin-2-amine and 4-{7-(2-Dimethylamino-1,1-dimethylethyl)-2-(4-fluorophenyl)imidazo[1,2-a]pyridin-3-yl}pyrimidin-2-amine shown above were made as described in Examples 1,2 and 3 from Intermediate I by conversion of the alcohol group to the corresponding mesylate, displacement of the mesylate group by nitrile anion followed by reduction of the nitrile group to an amine and reductive amination of the amine generated to the dimethyl amine group.

Scheme 3:

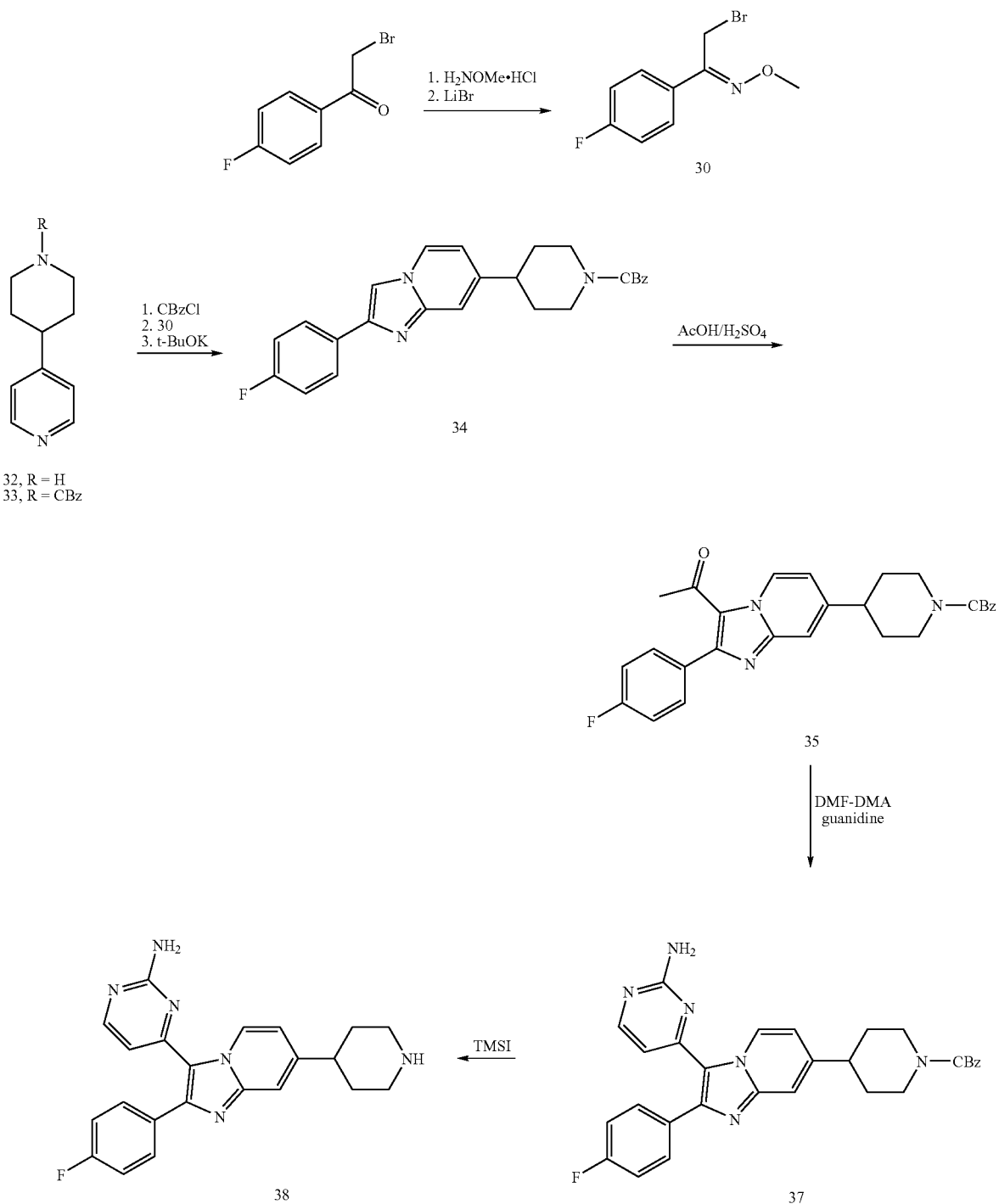

A different method of preparing imidzopyridines is shown above. The procedure is described in detail in Example 5. Oxime made from α-bromo ketone and O-methylhydroxylamine is cyclized with a pyridine analog in the presence of a base such as potassium tert-butoxide. The resulting imidazopyridine could be acylated at the 3-position with a reagent such as acetic acid-sulfuric acid and treated with DMF-DMA followed by guanidine and a base such as sodium methoxide to form the core structure 37 shown above Deprotection of the CBZ group followed by alkylation of the piperidine nitrogen gives the desired product.

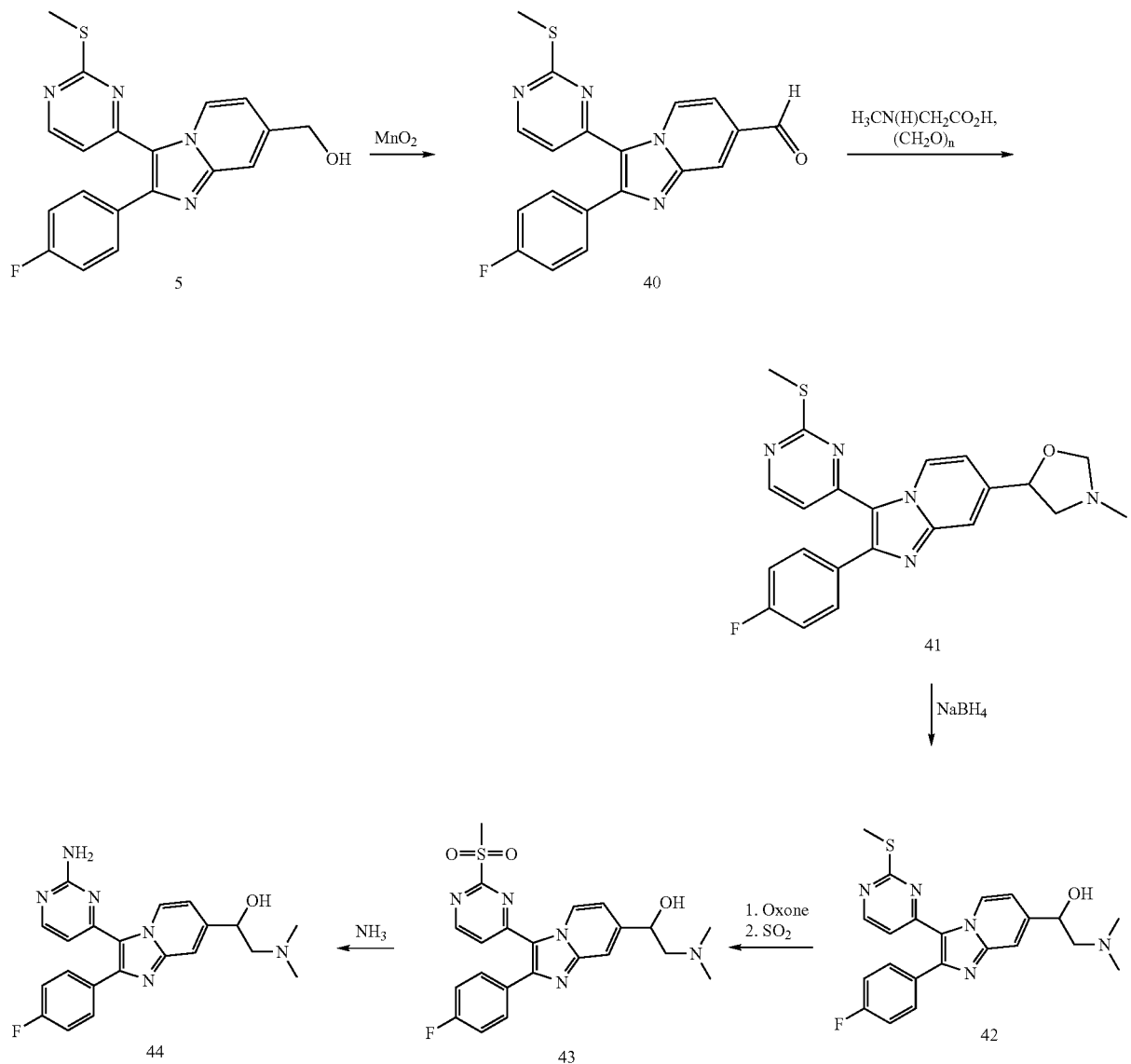

Intermediate 1 is oxidized with manganese dioxide to give the aldehyde that could be condensed with formaldehyde and reduced with sodium borohydride to give an amino alcohol. The sulfide of the pyrimidine group could be converted to the desired amino group by oxidation to the sulfone and displacement of the sulfone with ammonia as shown in the previous cases.

The following Examples are provided to illustrate the invention and are not to be construed as limiting the scope of the invention in any manner.

EXAMPLE 1

4-[7-(2-Aminoethyl)-2-(4-fluorophenyl)imidazo[1,2-a]pyridin-3-yl]pyrimidin-2-amine (24)

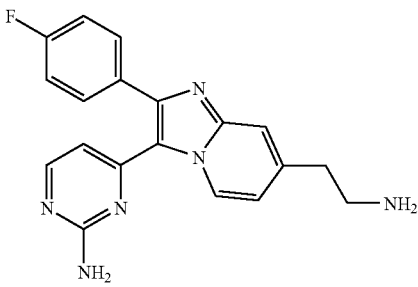

Step 1: 4-Methyl-2-(methylthio)pyrimidine (2)

A 22 L round bottom flask equipped with an air stirrer, heating mantle, thermometer, and reflux condenser was charged with toluene (12 L), 2-mercapto-4-methylpyrimidine hydrochloride (1) (900 g, 5.53 mol), diisopropylethylamine (1.07 kg, 8.30 mol), and N,N-dimethylformamide dimethyl acetal (1.61 kg, 12.7 mol). The reaction mixture was heated to reflux for 3.5 hours, and then the red solution was concentrated under reduced pressure to remove toluene, methanol, and some N,N-dimethylformamide. The residue was then treated with ethyl acetate (2 L), water (2 L), and enough 10% (w/v) aqueous sodium bisulfate solution to reach a pH of 4.5. After mixing, the organic layer was siphoned into a separate container, and the aqueous layer was extracted with additional ethyl acetate (2×2 L). All organic extracts were combined, dried over sodium sulfate, and concentrated under reduced pressure to yield ~1 L of a red oil, which was then purified by vacuum distillation at <1 mm Hg. Fractions that distilled off are as follows: T=30°-50° C.: ~100 mL ethyl acetate and N,N-dimethylformamide; T=60°-70° C.: 436.8 g product +14.5 g N,N-dimethylformamide; T=68°-72° C.: 267.4 g of pure product. Identity and purity of each fraction was determined by $^1$H NMR. Fractions 2 and 3 were combined and used in the next step without further purification. Yield of 2: 704.2 g (91%). $^1$H NMR (400 MHz, CDCl$_3$) δ 2.38 (s, 3H), 2.49 (s, 3H), 6.75 (d, J=5.2 Hz, 1H), 8.29 (d, J=5.2 Hz, 1H). MS (ESI+) 141.1.

Step 2: 2-[2-(Methylthio)pyrimidin-4-yl]-1-(4-fluorophenyl)ethanone+enol tautomer (3)

Sulfide 2 (1.00 g, 7.13 mmol) was dissolved in 15 mL tetrahydrofuran in a 3-neck, 50 mL round-bottom flask equipped with a magnetic stir bar, thermometer, and nitrogen inlet. The solution was stirred under nitrogen at −78° C. in a dry ice/isopropanol bath. Lithium diisopropylamide (15 mmol, 7.5 mL of a 2.0 M solution in heptane/tetrahydrofuran/ ethylbenzene) was then added in small portions, during which reaction temperature was maintained <−65° C. After stirring for an additional hour at <−75° C., the reaction mixture was treated with a cooled solution of methyl 4-fluorobenzoate (1.21 g, 7.85 mmol) in tetrahydrofuran dropwise via addition funnel over 15 min, during which reaction temperature was maintained at <−55° C. The reaction mixture was allowed to warm to room temperature while being stirred overnight, and was then diluted with a saturated aqueous ammonium chloride solution (50 mL), and extracted with ethyl acetate (3×50 mL). Organic extracts were pooled, dried over sodium sulfate, and concentrated under reduced pressure to give 2.15 g of crude solid, which was triturated with pentane (50 mL) and filtered. After drying under vacuum at 50° C. overnight, the remaining solid (1.05 g) was 77% pure by HPLC, and not purified further. Yield of 3: 809 mg (43%). $^1$H NMR (400 MHz, CDCl$_3$) δ enol tautomer (major): 2.60 (s, 3H), 5.91 (s, 1H), 6.63 (d, J=5.6 Hz, 1H), 7.14 (m, 2H), 7.82 (m, 2H), 8.29 (d, J=5.2 Hz, 1H); ketone tautomer (minor): 2.51 (s, 3H), 4.34 (s, 2H), 6.97 (d, J=4.8 Hz, 1H), 7.14 (m, 2H), 8.07 (m, 2H), 8.45 (d, J=5.2 Hz, 1H). MS (ESI+) 263.1.

Step 3: 2-Bromo-2-[2-(methylthio)pyrimidin-4-yl]-1-(4-fluorophenyl)ethanone (4)

Ketone/enol mixture 3 (219 g, 0.833 mol) was slurried in carbon tetrachloride (1.5 L) in a 12 L round bottom flask equipped with an air stirrer and nitrogen inlet. This was followed by the addition of tetra-n-butylammonium tribromide (402 g, 0.833 mol) in three portions, then methylene chloride (3 L). After stirring at room temperature for 2 hours under nitrogen, the reaction mixture was diluted with an aqueous solution of saturated sodium bicarbonate (3 L), and stirred for an additional 30 min. The aqueous layer was then siphoned off, and the organic layer was dried over sodium sulfate, and concentrated under reduced pressure to yield a dark red, viscous oil, which was not purified further. Assumed yield of 4: 284 g (100%). $^1$H NMR (400 Mz, CDCl$_3$) δ 2.43 (s, 3H), 6.19 (s, 1H), 7.09 (t, J=8.4 Hz, 2H), 7.35 (d, J=4.8 Hz, 1H), 8.01 (m, 2H), 8.51 (m, 1H). MS (2AWS1) (ESI+) 341.0.

Step 4: {2-(4-Fluorophenyl)-3-[(2-methylthio)pyrimidin-4-yl]imidazo[12-a]-pyridin-7-yl}methanol (5)

Bromide 4 (assumed quantity based on 100% yield of the previous step: 284 g, 0.833 mol) was suspended in ethanol (3 L) in a 12 L round-bottom flask equipped with an air stirrer, thermometer, and nitrogen inlet. The reaction mixture was then charged with 2-amino-4-hydorxymetyhylpyridine (103 g, 0.833 mol), and 4 Åmolecular sieves (300 mL, activated at 175° C. overnight in a vacuum oven), and was then heated overnight at 60° C. The reaction mixture was then filtered while hot to remove the molecular sieves, and the resulting filtrate was allowed to cool to room temperature. The solid that precipitated out the filtrate was then collected with a fritted funnel; this solid was found to be 95% pure product by $^1$H NMR. After drying in a vacuum oven at 40° C. overnight, 92 g of 5 was obtained (fraction #1). The resulting filtrate was then concentrated under reduced pressure to yield a brown oil, which was then triturated with ethanol (200 mL). The resulting precipitate was collected on a fritted funnel, and found by $^1$H NMR to be a mixture of desired product and 2-amino-4-hydroxymethylpyridine (or its HBr salt). The filter cake was washed with water (500 mL), and then dried in a vacuum oven at 50° C. for 3 hours. The filter cake crystallized when recombined with filtrate and washings, and was filtered on a flitted funnel, was then air dried, and then washed with pentane (500 mL). After drying in a vacuum oven at 40° C. overnight, 41 g of 5 was obtained (fraction #2). Yield of 5: 133 g (43% over two steps). $^1$H NMR (400 MHz, CDCl$_3$) δ 2.56

(s, 3H), 4.60 (s, 2H), 6.85 (d, J=5.2 Hz, 1H), 7.07 (d, J=7.2 Hz, 1H), 7.27 (t, J=8.8 Hz, 2H), 7.62 (m, 3H), 8.43 (d, J=5.2 Hz, 1H), 9.30 (d, J=7.2 Hz, 1H). MS (ESI+) 367.2.

Step 5: {2-(4-Fluorophenyl)-3-[(2-methylthio)pyrimidin-4-yl]imidazo[1,2-a]-pyridin-7-yl}(methanesulfonyloxy)methane (6)

Imidazopyridine 5 (161 g, 0.439 mol) was added to a 2 L, 3-neck round-bottom flask equipped with an air stirrer, nitrogen inlet, thermometer, and addition funnel. This was followed by the addition of tetrahydrofuran (500 mL) and triethylamine (66.7 g, 0.659 mol). The reaction mixture was then cooled to 5° C. in an ice water bath. Methanesulfonyl chloride (55.4 g, 0.484 mol) was then added dropwise, during which the reaction temperature was maintained at <15° C. Once the addition was completed, the ice bath was removed, .the reaction mixture stirred at room temperature for 1 hour. The reaction mixture was then diluted with water (500 mL), transferred to a separatory funnel, and then extracted with ethyl acetate (2×500 mL). The aqueous layer was then diluted with aqueous saturated sodium chloride solution (500 mL) and extracted with additional ethyl acetate (500 mL). All organic fractions were pooled, dried over sodium sulfate, and concentrated under reduced pressure to yield a solid that was triturated with pentane (500 mL) to remove residual solvent, and the dried in a vacuum oven overnight at 40° C. Yield of 6: 165.2 g (85%). $^1$H NMR (400 MHz, CDCl$_3$) 2.64 (s, 3H), 3.07 (s, 3H), 5.32 (s, 2H), 6.82 (d, J=5.2 Hz, 1H), 7.03 (dd, J=7.2, 1.6 Hz, 1H), 7.14 (t, J=8.4 Hz, 2H), 7.61 (m, 2H), 7.73 (s, 1H), 8.32 (d, J=5.6 Hz, 1H), 9.59 (d, J=7.2 Hz, 1H). MS (ESI+) 445.2.

Step 6: {2-(4-Fluorophenyl)-3-[(2-methylthio)pyrimidin-4-yl]imidazo[1,2-a]-pyridin-7-yl}acetonitrile (7)

To a 1.0 L round-bottom flask was added mesylate 6 (7.40 g, 16.6 mmol), methylene chloride (200 mL), and n-Bu$_4$NCN (4.47 g, 16.6 mmol). After stirring at room temperature for 12 hours, the reaction mixture was loaded onto a silica plug and chromatographed with 500 mL heptane, then 2.0 L 50:50 ethyl acetate:heptane, and then 4.0 L ethyl acetate, collecting 500 mL fractions. Fractions containing desired product (3 through 5) were pooled and concentrated under reduced pressure. Yield of 7: 4.20 g (67%). $^1$H NMR (500 MHz, CDCl$_3$) δ 2.65 (s, 3H), 3.88 (s, 2H), 6.83 (d, J=5.5 Hz, 1H), 6.95 (dd, J=7.5, 2.0 Hz, 1H), 7.15 (t, J=8.8 Hz, 2H), 7.62 (m, 2H), 7.69 (s, 1H), 8.32;(d, J=5.0 Hz, 1H), 9.61 (d, J=7.5 Hz, 1H). MS (ESI+) 376.2.

Step 7: {2-(4-Fluorophenyl)-3-[2-(methanesulfonyl)pyrimidin-4-yl]imidazo[1,2-a]pyridin-7-yl}acetonitrile (22)

A 500 mL round bottom flask containing sulfide 7 (1.00 g, 2.66 mmol) was charged with methanol (150 mL), then a 150 mL aqueous solution of Oxone (10.0 g, 16.4 mmol), and then acetone (150 mL), then acetone (150 mL). After stirring for 6 hours at room temperature, the reaction mixture was poured into a separatory funnel, then diluted with water (250 mL), and then extracted with 250 mL ethyl acetate; the aqueous layer was then extracted with an additional 2×100 mL ethyl acetate. The organic fractions were pooled, dried over Na$_2$SO$_4$, filtered, and then concentrated under reduced pressure. Yield of 22: 980 mg (91%). $^1$H NMR (400 MHz, CDCl$_3$) δ 3.40 (s, 3H), 3.91 (s, 2H), 7.07 (d, J=7.6 Hz, 1H), 7.20 (t, J=8.2 Hz, 2H), 7.31 (d, J=5.6 Hz, 1H), 7.61 (m, 2H), 7.77 (s, 1H), 8.54 (d, J=5.6 Hz, 1H), 9.92 (d, J=7.6 Hz, 1H). MS (ESI+) 408.2.

Step 8: 2{2-(4-Fluorophenyl)-3-[2-(methanesulfonyl)pyrimidin-4-yl]-imidazo[1,2-a]pyridin-7-yl}ethanamine (23)

A 300 mL pressure bottle containing nitrile 22 (980 mg, 2.41 mmol) was charged with ethanol (18 mL), chloroform (2 mL), and then PtO$_2$ (200 mg, 0.881 mmol). The pressure bottle was then sealed, then charged with 50 psi hydrogen, and the reaction mixture was allowed to stir at room temperature for 12 hours, after which additional PtO$_2$ (500 mg, 1.14 mmol) was added, and an the pressure bottle was charged with an additional 50 psi hydrogen then sealed, and the reaction mixture was stirred at room temperature for 3 hours. At this point, TLC analysis showed the reaction to be complete. The reaction mixture was then filtered through successive 0.45 □m Gelman nylon acrodiscs. The filtrate was then concentrated under reduced pressure and carried onto the next step without further purification. Crude yield of 23: 1.20 g (121%). MS (ESI+) 412.2.

Step 9: 4[7-(2-Aminoethyl)-2-(4-fluorophenyl)imidazo[1,2-a]pyridin-3-yl]-pyrimidin-2-amine (24)

A 300 mL pressure bottle was charged with sulfone 23 (1.20 g crude, theoretically 1.00 g, 2.41 mmol) then THF (50 mL), and was then chilled to −40° C. in a dry ice/isopropanol bath. Excess ammonia gas (19.1 g) was then bubbled into the reaction mixture over 20 minutes. The pressure bottle was then sealed, and the reaction mixture was allowed to warm to room temperature while stirring for 6 hours. The reaction mixture was then concentrated under reduced pressure, then dissolved in a minimum volume of CH$_2$Cl$_2$, then loaded onto a 40 g Isco RediSep normal phase silica cartridge, and purified on an Isco OptiX10 CombiFlash instrument using a gradient that started at 100% methylene chloride and ended at 90% methylene chloride, 9% methanol, 1% concentrated ammonium hydroxide. Fractions containing desired product were pooled and concentrated under reduced pressure. Yield of 24: 214 mg (26% over two steps). $^1$H NMR (500 MHz, CDCl$_3$) δ 2.87 (t, J=7.0 Hz, 2H), 3.08 (t, J=7.0 Hz, 2H), 5.14 (bs, 2H), 6.53 (d, J=5.0 Hz, 1H), 6.82 (dd, J=7.0, 1.5 Hz, 1H), 7.14 (m, 2H), 7.51 (s, 1H), 7.65 (m, 2H), 8.13 (d, J=5.5 Hz, 1H), 9.45 (d, J=7.0 Hz, 1H). MS (ESI+) 349.3.

EXAMPLE 2

4{7-[2-(Dimethylamino)ethyl]-2-(4-fluorophenyl)imidazo[1,2-a]pyridin-3-yl}-pyrimidin-2-amine (25)

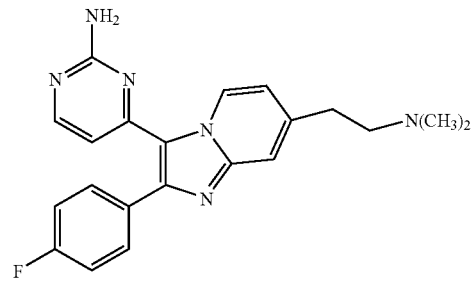

Step 1: 4-{7-[2-(Dimethylamino)ethyl]-2-(4-fluorophenyl)imidazo[1,2-a]pyridin-3-yl}pyrimidin-2-amine (25)

A 28 mL Pyrex-Plus tube containing the product of Example 1, Step 9 (30 mg, 0.086 mmol) was charged with methanol (1.0 mL), then acetic acid (33 μL), then formaldehyde (28 mg of a 37% aqueous solution, 0.34 mmol), then NaBH$_3$CN (431 μL of a 1.0M solution in THF, 0.431 mmol), and stirred at room temperature for 12 hours. A separate 28 mL Pyrex-Plus tube containing the product of Example 1, Step 9 (70 mg, 0.20 mmol) was charged with methanol (2.0 mL), then acetic acid (67 μL), then formaldehyde (65 mg of a 37% aqueous solution, 0.80 mmol), then NaBH$_3$CN (1.00 mL of a 1.0M solution in THF, 1.00 mmol), and stirred at room temperature for 2 hours. Both reaction mixtures were then combined, along with 50 mgs of crude product prepared previously then concentrated under reduced pressure, then dissolved in a minimum volume of methylene chloride, then injected directly onto a 40 g Isco RediSep normal phase silica cartridge, and purified on an Isco OptiX10 CombiFlash instrument using a gradient that started at 100% methylene chloride and ended at 90% methylene chloride, 9% methanol, 1% concentrated ammonium hydroxide. Fractions containing desired product were pooled and concentrated under reduced pressure, yielding 110 mg of dimethylamine 25. This sample was dissolved in 4 mL methanol and purified on an HPLC column, from 4×1.0 mL injections, using a gradient that started at 40% methanol and 60% water and ended at 100% methanol. Fractions containing desired product were pooled and concentrated under reduced pressure. Quantity isolated of 25: 68 mg. $^1$H NMR (500 MHz, CDCl$_3$) δ 2.33 (s, 6H), 2.64 (t, J=7.8 Hz, 2H), 2.89 (t, J=7.8 Hz, 2H), 5.11 (bs, 2H), 6.52 (d, J=5.5 Hz, 1H), 6.83 (dd, J=7.0, 2.0 Hz, 1H), 7.14 (m, 2H), 7.52 (dd, J=1.8, 0.5 Hz, 1H), 7.65 (m, 2H), 8.12 (d, J=5.5 Hz, 1H), 9.44 (dd, J=7.5, 0.5 Hz, 1H). MS (ESI+) 377.4.

EXAMPLE 3

4-[7-(2-Amino-1,1-dimethylethyl)-2-(4-fluorophenyl)imidazo[1,2-a]pyridin-3-yl]-pyrimidin-2-amine (28)

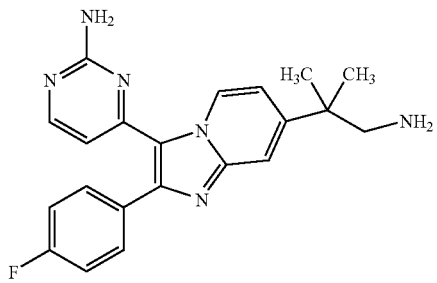

Step 1: 2-{2-(4-Fluorophenyl)-3-[(2-methylsulfanyl)pyrimidin-4-yl]imidazo-[1,2-a]pyridin-7-yl}-2-methylpropanenitrile (8)

To a 500 mL round bottom flask was added nitrile 7 (3.70 g, 9.85 mmol) and THF (200 mL), and the flask was cooled in an ice-water bath. Sodium hydride (1.18 g of 60% w/w sample in mineral oil, 29.6 mmol) was then added in portions, followed by the addition of methyl iodide (3.08 g, 21.7 mmol). The reaction mixture was allowed to warm to room temperature. After stirring for 30 minutes, the reaction was quenched with 100 mL water, and then extracted into 3×200 mL ethyl acetate. The organic fractions were pooled, dried over Na$_2$SO$_4$, filtered, and concentrated under reduced pressure. The resulting residue was dissolved in a minimum volume of methylene chloride, then loaded onto a silica plug and chromatographed with 1.0 L heptane, and then 2.0 L 50:50 ethyl acetate:heptane, collecting 500 mL fractions. Fractions containing desired product (2 through 4) were pooled and concentrated under reduced pressure. Yield of 8: 3.21 g (81%). $^1$H NMR (400 MHz, CDCl$_3$) δ 1.80 (s, 6H), 2.64 (s, 3H), 6.82 (d, J=5.6 Hz, 1H), 7.11 (d, J=7.3 Hz, 1H), 7.14 (t, J=8.6 Hz, 2H), 7.61 (m, 2H), 7.77 (s, 1H), 8.31 (d, J=5.6 Hz, 1H), 9.61 (d, J=7.4 Hz, 1H). MS (ESI+) 404.2.

Step 2: 2-{2-(4-Fluorophenyl)-3-[2-(methylsulfonyl)pyrimidin-4-yl]imidazo[1,2-a]pyridin-7-yl}-2-methylpropanenitrile (26)

To a 1.0 L round bottom flask was added sulfide 8 (2.20 g, 5.45 mmol), then methanol (100 mL), then a 100 mL aqueous solution of Oxone (10.0 g, 16.4 mmol), then acetone (100 mL). After stirring for 12 hours at room temperature, the reaction mixture was poured into a separatory funnel, then diluted with water (100 mL), and then extracted with 4×200 mL ethyl acetate. The organic fractions were pooled, dried over Na$_2$SO$_4$, filtered, and then concentrated under reduced pressure. Yield of 26: 2.10 g (89%). $^1$H NMR (500 MHz, CDCl$_3$) δ 1.84 (s, 6H), 3.43 (s, 3H), 7.25 (m, 3H), 7.34, (d, J=5.5 Hz, 1H), 7.65 (m, 2H), 7.90 (dd, J=2.0, 1.0 Hz, 1H), 8.57 (d, J=5.5 Hz, 1H), 9.97 (dd, J=7.5, 1.0 Hz, 1H). MS (ESI+) 436.2.

Step 3: 2-[3-(2-Aminopyrimidin-4yl)-2-(4-fluorophenyl)imidazo[1,2-a]pyridin-7-yl]-2-methylpropanenitrile (27)

A 300 mL pressure bottle was charged with sulfone 26 (1.10 g, 2.53 mmol), then THF (100 mL), and was then chilled to −40° C. in a dry ice/isopropanol bath. Excess ammonia gas (49 g) was then bubbled into the reaction mixture over 20 minutes. The pressure bottle was then sealed, and the reaction mixture was allowed to warm to room temperature while stirring for 72 hours. The reaction mixture was diluted with water (200 mL), and then extracted into 3×200 mL ethyl acetate. The organic fractions were pooled, dried over Na$_2$SO$_4$, filtered, and then concentrated under reduced pressure. Yield of 27: 750 mg (80%). $^1$H NMR (500 MHz, CDCl$_3$) δ 1.82 (s, 6H), 5.15 (bs, 2H), 6.56 (d, J=5.5 Hz, 1H), 7.09 (dd, J=7.5, 2.0 Hz, 1H), 7.15 (t, J=8.8 Hz, 2H), 7.66 (m, 2H), 7.77 (d, J=2.0, 1.0 Hz, 1H), 8.17 (d, J=5.5 Hz, 1H), 9.45 (dd, J=7.5, 1.0 Hz, 1H). MS (ESI+) 373.4.

Step 4: 4-[7-(2-Amino-1,1-dimethylethyl)-2-(4-fluorophenyl)imidazo[1,2-a]-pyridin-3-yl]pyrimidin-2-amine (28)

A 100 mL round bottom flask containing nitrile 27 (700 mg, 1.88 mmol) in THF (25 mL) was charged with lithium aluminum hydride (285 mg, 7.52 mmol). After stirring at room temperature for 45 minutes, the reaction mixture was poured into an 1.0 L Erlenmeyer flask and quenched with 200 mL ethyl acetate, 10 mL water, sodium sulfate, and an excess of 2:1 Na$_2$SO$_4$ 10H$_2$O:celite. The mixture was filtered, then concentrated under reduced pressure, and then dissolved in a minimum volume of CH$_2$Cl$_2$, then loaded onto a 40 g Isco RediSep normal phase silica cartridge, and purified on an Isco OptiX10 CombiFlash instrument using a gradient that started at 100% methylene chloride and ended at 90% methylene chloride, 9% methanol, 1% concentrated ammonium hydroxide. Fractions containing desired product were pooled and concentrated under reduced pressure. Yield of 28: 196 mg (28%). $^1$H NMR (500 MHz, CDCl$_3$) δ 1.38 (s, 6H), 2.89 (s, 2H), 5.14 (bs, 2H), 6.54 (d, J=5.5 Hz, 1H), 6.97 (dd, J=7.5, 2.0 Hz, 1H), 7.14 (m, 2H), 7.65 (m, 3H), 8.13 (d, J=5.5 Hz, 1H), 9.46 (dd, J=7.5, 0.5 Hz, 1H). MS (ESI+) 377.2.

EXAMPLE 4

4-[7-(2-Dimethylamino-1,1-dimethylethyl)-2-(4-fluorophenyl)imidazo[1,2-a]pyridin-3-yl]pyrimidin-2-amine (29)

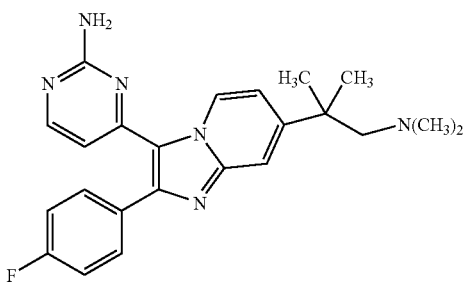

A 28 mL Pyrex-Plus tube containing amine 28 (Example 3, 170 mg, 0.452 mmol) was charged with methanol (2.0 mL), then acetic acid (170 □L), then formaldehyde (110 mg of a 37% aqueous solution, 1.35 mmol), then NaBH$_3$CN (2.26 mL of a 1.0M solution in THF, 2.26 mmol). After stirring at room temperature for 1 hour, the reaction mixture was injected directly onto a 40 g Isco RediSep normal phase silica cartridge, and purified on an Isco OptiX10 CombiFlash instrument using a gradient that started at 100% methylene chloride and ended at 90% methylene chloride, 9% methanol, 1% concentrated ammonium hydroxide. Fractions containing desired product were pooled and concentrated under reduced pressure, yielding 140 mg of dimethylamine 29. This sample was dissolved in 5 mL methanol and purified on an HPLC column, from 5×1.0 mL injections, using a gradient that started at 40% methanol and 60% water and ended at 100% methanol. Fractions containing desired product were pooled and concentrated under reduced pressure. Yield of 29: 104 mg (57%). $^1$H NMR (500 MHz, CDCl$_3$) δ 1.39 (s, 6H), 2.15 (s, 6H), 2.54 (s, 2H), 6.54 (d, J=5.5 Hz, 1H), 7.06 (dd, J=7.3, 2.0 Hz, 1H), 7.13 (m, 2H), 7.67 (m, 3H), 8.12 (d, J=5.5 Hz, 1H), 9.44 (dd, J=7.3, 0.5 Hz, 1H). MS (ESI+) 405.3.

EXAMPLE 5

4-{2-(4-Fluorophenyl)-7-(piperidin-4-yl)imidazo[1,2-a]pyridin-3-yl}pyrimidin-2-amine (38)

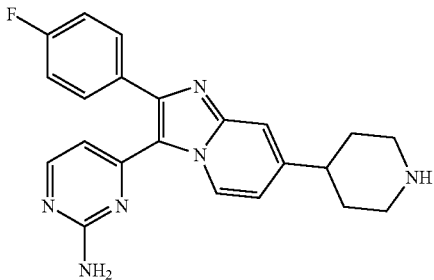

Step 1: 2-Bromo-1-(4-fluorophenyl)ethanone O-methyloxime (30)

A 2.0 L round bottom flask was charged with 4-fluorophenacyl bromide (97.6 g, 450 mmol), then methanol (750 mL), then O-methylhydroxylamine hydrochloride (75.1 g, 899 mol), and the mixture was heated to 65° C. for 2 hours. The reaction mixture was then concentrated under reduced pressure, charged with acetone (750 mL), and lithium bromide (195 g, 2.25 mol), and heated to 60° C. for 15 hours. The reaction mixture was then concentrated under reduced pressure, suspended in 1.0 L methylene chloride, and washed with 3×200 mL water. The aqueous extracts were then pooled and back-extracted with 2×200 mL methylene chloride. All organic extracts were then pooled, dried over Na$_2$SO$_4$, filtered, and concentrated under reduced pressure to yield O-methyloxime 30. Yield of 30: 92.3 g (83%). $^1$H NMR (500 MHz, CDCl$_3$) δ 4.10 (s, 3H), 4.35 (s, 2H), 7.11 (t, J=8.8 Hz, 2H), 7.72 (m, 2H). MS (ESI+) 246.0.

Step 2: 4-Piperidin-4-ylpyridine (32)

This compound is commercially available from ChemBridge Corp., San Diego, Calif.

Step 3: Benzyl 4-pyridin-4-ylpiperidine-1-carboxylate (33)

A 10 mL round bottom flask was charged with piperidine 32 (500 mg, 3.08 mmol), and then triethylamine (314 mg, 3.10 mmol), and then CbzCl (529 mg, 3.10 mmol), and the reaction mixture was allowed to stir at room temperature for 12 hours. The reaction mixture was then poured into 50 mL of an aqueous solution saturated with NaHCO$_3$ and extracted with 3×50 mL of methylene chloride. The organic fractions were pooled, dried over Na$_2$SO$_4$, filtered, concentrated under reduced pressure, and not purified further. Crude yield of 33: 900 mg (99%). $^1$H NMR (500 MHz, CDCl$_3$) δ 1.87 (m, 2H), 2.30 (m, 2H), 2.69 (m, 1H), 2.91 (bs, 2H), 4.37 (bs, 2H), 5.17 (m, 2H), 7.13 (d, J=6.3 Hz, 2H), 7.39 (m, 5H), 8.54 (d, J=6.3 Hz, 2H).

Step 4: Benzyl 4[2-(4-fluorophenyl)imidazo[1,2-a]pyridin-7-yl]piperidine-1-carboxylate (34)

A 500 mL round bottom flask was charged with crude pyridine 33 (8.20 g, 27.7 mmol), acetone (300 mL), and O-methyloxime 30 (6.8 g, 27.7 mmol), and the reaction mixture was allowed to stir at room temperature for 12 hours, after which thin-layer chromatography testing suggested that pyridinyl salt formation was complete. The reaction was then concentrated under reduced pressure in a 500 mL round bottom flask, and charged with methanol (200 mL), additional pyridinyl salt prepared previously (600 mg), and potassium tert-butoxide (3.90 g, 34.6 mmol). The resulting mixture was heated to 65° C. for 4 hours. The reaction mixture was then poured into 400 mL of an aqueous solution saturated with NaHCO$_3$ and extracted with 3×250 mL of methylene chloride. The organic fractions were pooled, dried over Na$_2$SO$_4$, filtered, concentrated under reduced pressure, then dissolved in a minimum volume of CH$_2$Cl$_2$, then loaded onto 3×40 g Isco RediSep normal phase silica cartridges, and purified on an Isco OptiX10 CombiFlash instrument using a gradient that started at 100% methylene chloride and ended at 90% methylene chloride, 9% methanol, and 1% concentrated ammonium hydroxide. Fractions containing the desired product were pooled and concentrated under reduced pressure; fractions containing impure product were pooled, concentrated under reduced pressure, then dissolved in a minimum volume of CH$_2$Cl$_2$, and loaded onto 2×40 g Isco RediSep normal phase silica cartridges, and purified on an Isco OptiX10 CombiFlash instrument using a gradient which started at 100% heptane and ended at 100% ethyl acetate. This process was repeated once on the remaining impure product. Yield of 34: 3.10 g (26%). $^1$H NMR (500 MHz, CDCl$_3$) δ 1.50 (m, 2H), 1.76 (m, 2H), 2.55 (m, 1H), 2.77 (bs, 2H), 4.45 (bs, 2H), 5.04 (s, 2H), 6.48 (d, J=5.3 Hz, 1H), 6.96 (t, J=8.8 Hz, 2H), 7.24 (m, 6H), 7.57 (s, 1H), 7.76 (m, 2H), 7.86 (d, J=7.1 Hz, 1H). MS (ESI+) 430.2.

Step 5: Benzyl 4-[3-acetyl-2-(4-fluorophenyl)imidazo[1,2-a]pyridin-7-yl]piperidine-1-carboxylate (35)

Imidazopyridine 34 (290 mg, 0.675 mmol) was dissolved in acetic (50 mL) in a 250 mL round bottom flask. Three drops of sulfuric acid were then added, and the reaction was heated to 140° C. for 24 hours. The reaction was then concentrated under reduced pressure, then diluted with both ethyl acetate and saturated sodium bicarbonate solution, and extracted repeatedly into ethyl acetate. Organic fractions were pooled, dried over sodium sulfate, filtered, and concentrated under reduced pressure. The crude product was then dissolved in 5 mL methylene chloride, then loaded onto a 40 g Isco RediSep normal phase silica cartridge, and purified on an Isco OptiX10 CombiFlash instrument using a gradient that started at 100% heptane and ended at 100% ethyl acetate. Fractions containing desired product were pooled and concentrated under reduced pressure. Yield of 35: 180 mg (56%). $^1$H NMR (400 MHz, CDCl$_3$) δ 1.67 (m, 2H), 1.92 (m, 2H), 2.17 (s, 3H), 2.81 (m, 1H), 2.93 (bs, 2H), 4.38 (bs, 2H), 5.16 (s, 2H), 6.48 (d, J=7.2 Hz, 1H), 6.96 (t, J=8.8 Hz, 2H), 7.24 (m, 5H), 7.57 (s, 1H), 7.76 (m, 2H), 7.86 (d, J=7.2 Hz, 1H). MS (ESI+) 472.2.

Step 6: Benzyl 4-[3-(2-aminopyrimidin-4-yl)-2-(4-fluorophenyl)imidazo[1,2-a]pyridin-7-yl]piperidine-1-carboxylate (37)

A 28 mL Pyrex Plus tube was charged with ketone 35 (420 mg, 0.89 mmol), DMFDMA (530 mg, 4.45 mmol) and toluene (10 mL). The reaction was heated to 100° C. for 7 hours, after which more DMFDMA (530 mg, 4.45 mmol) was added, and the reaction was allowed to heat at 100° C. for 12 more hours. The reaction was then concentrated under reduced pressure, and then dissolved in 1-propanol (20 mL). The reaction was then charged with guanidine-HCl (128 mg, 1.34 mmol) and sodium methoxide (305 □L of a 25% (w/w) solution in methanol, 1.34 mmol), and the reaction was heated to 80° C. for 18 hours. The reaction was then concentrated under reduced pressure, then dissolved in 10 mL CH$_2$Cl$_2$, then loaded onto a 40 g Isco RediSep normal phase silica cartridge, and purified on an Isco OptiX10 CombiFlash instrument using a gradient that started at 100% heptane and ended at 100% ethyl acetate. Fractions containing desired product were pooled and concentrated under reduced pressure. Yield of 37: 190 mg (41% over both steps). $^1$H NMR (400 MHz, CDCl$_3$) δ 1.62 (m, 2H), 1.88 (m, 2H), 2.74 (m, 1H), 2.91 (m, 2H), 4.34 (bs, 2H), 5.14 (s, 2H), 5.21 (s, 2H), 6.48 (d, J=5.2 Hz, 1H), 6.74 (d, J=7.2 Hz, 1H), 7.09 (t, J=8.8 Hz, 2H), 7.34 (m, 5H), 7.44 (bs, 1H), 7.60 (m, 2H), 8.08 (d, J=5.2 Hz, 1H), 9.40 (d, J=7.2 Hz, 1H). MS (ESI+) 523.7.

Step 7: 4[2-(4-Fluorophenyl)-7-(piperidin-4-yl)imidazo[1,2-a]pyridin-3-yl]pyrimidin-2-amine (38)

Benzyl carbonate 37 (190 mg, 0.36 mmol) was slurried in CH$_3$CN (5 mL) in a 28 mL Pyrex Plus tube. TMSI (720 mg, 3.6 mmol) was then added, and the reaction was allowed to stir at room temperature for 2 hours. The reaction was then concentrated under reduced pressure. The crude product was then dissolved in 10 mL CH$_2$Cl$_2$, plus a few drops of methanol, then loaded onto a 40 g Isco RediSep normal phase silica cartridge, and purified on an Isco OptiX10 CombiFlash instrument using a gradient that started at 100% methylene chloride and ended at 90% methylene chloride, 9% methanol, 1% concentrated ammonium hydroxide. Fractions containing desired product were pooled and concentrated under reduced pressure. Yield of 38: 140 mg (100%). $^1$H NMR (400 MHz, CDCl$_3$) δ 1.67 (m, 2H), 1.84 (m, 2H), 2.67 (m, 1H), 2.74 (m, 2H), 3.18 (m, 2H), 5.03 (s, 2H), 6.44 (d, J=5.2 Hz, 1H), 6.77 (d, J=7.2 Hz, 1H), 7.05 (t, J=8.8 Hz, 2H), 7.43 (bs, 1H), 7.56 (m, 2H), 8.04 (d, J=5.2 Hz, 1H), 9.36 (d, J=7.2 Hz, 1H). MS (ESI+) 389.2.

EXAMPLE 6

4[2-(4-Fluorophenyl)l-7-(1-methylpiperidin-4-yl)imidazo[1,2-a]pyridin-3-yl]pyrimidin-2-amine (39)

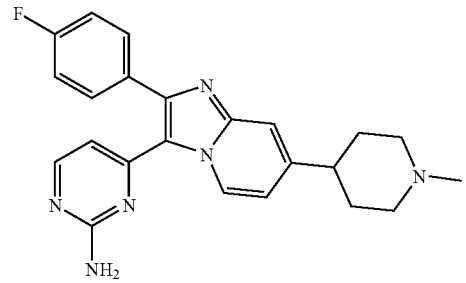

Step 1: 4-[2-(4-Fluorophenyl)l-7-(1-methylpiperidin-4-yl)imidazo[1,2-a]pyridin-3-yl]pyrimidin-2-amine (39)

A 28 mL reaction tube containing N-protio piperidine 38 (140 mg, 0.36 mmol) was charged with methanol (7 mL), formaldehyde (88 mg of a 37% w/w solution, 1.1 mmol) then acetic acid (180 □L), then NaBH$_3$CN (4.0 mL of a 1.0 M solution in THF, 4.0 mmol), and the reaction was allowed to stir at room temperature for 20 minutes. The reaction was then injected directly onto a 40 g Isco RediSep normal phase silica cartridge, and purified on an Isco OptiX10 CombiFlash instrument using a gradient that started at 100% methylene chloride and ended at 100% methylene chloride and ended at 90% methylene chloride, 9% methanol, and 1% concentrated ammonium hydroxide. Fractions containing desired product were then pooled and concentrated under reduced pressure. The crude product (110 mg, 76%) was then dissolved in 3 mL of DMSO an injected in 0.5 mL increments onto a semi-prep reverse phase HPLC column, and purified with a gradient that started at 20% methanol and 80% water and ended at 100% methanol. Fractions containing pure desired product were pooled and concentrated under reduced pressure. Yield of pure 39: 60 mg (41%). $^1$H NNM (400 MHz, CDCl$_3$) δ 1.89 (m, 4H), 2.08 (t, J=11.6 Hz, 2H), 2.33 (s, 3H), 2.56 (m, 1H), 3.00 (bd, J=11.6 Hz, 2H), 5.11 (s, 2H), 6.49 (d, J=5.4 Hz, 1H), 6.82 (d, J=7.4 Hz, 1H), 7.10 (t, J=8.8 Hz, 2H), 7.49 (bs, 1H), 7.61 (m, 2H), 8.09 (d, J=5.4 Hz, 1H), 9.41 (d, J=7.4 Hz, 1H). MS (ESI+) 403.2.

EXAMPLE 7

1-[3-(2-Aminopyrimidin-4-yl)-2-(4-fluorophenyl)imidazo[1,2-a]pyridin-7-yl]-2-(dimethylamino)ethanol (44)

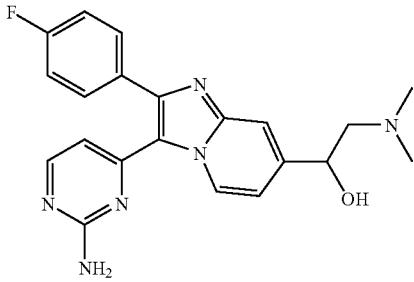

Step 1: 2-(4-Fluorophenyl)-3-[2-(methylthio)pyrimidin-4-yl]imidazo[1,2-a]pyridine-7-carbaldehyde (40)

A 1.0 L round bottom flask was charged with alcohol 5 (3.66 g, 9.99 mol), methylene chloride (750 mL), and $MnO_2$ (21.7 g, 250 mmol). After stirring at room temperature for 5 hours, the reaction was poured through a pad of celite, and the reaction flask was then rinsed with 750 mL methylene chloride and 500 mL ethyl acetate, and the rinses were also filtered through celite. The filtrate was then concentrated under reduced pressure and dried under vacuum, and not purified further. Yield of 40: 2.39 g (66%). $^1$H NMR (500 MHz, $CDCl_3$) δ 2.65 (s, 3H), 6.87 (d, J=5.5 Hz, 1H), 7.17 (t, J=9.0 Hz, 2H), 7.51 (d, J=7.5 Hz, 1H), 7.65 (m, 2H), 8.27 (s, 1H), 8.40 (d, J=5.5 Hz, 1H), 9.54 (d, J=7.5 Hz, 1H), 10.08 (s, 1H). MS (ESI+) 365.2.

Step 2: 2-(4-Fluorophenyl)-7-(3-methyl-1,3-oxazolidin-5-yl)-3-[2-(methylthio)pyrimidinyl]imidazo[1,2-a]pyridine (41)

A 250 mL round bottom flask equipped with a Dean Stark trap was charged with aldehyde 40 (1.44 g, 3.95 mmol), toluene (120 mL), sarcosine (710 mg, 7.97 mmol), and paraformaldehyde (600 mg, 20.0 mmol), and the reaction was heated under reflux for 12 hours, then concentrated under reduced pressure, dissolved in a minimum volume of acetone, and filtered through a 5 g silica cartridge, which was then washed with 80 mL of acetone. The filtrate was then concentrated under reduced pressure, and not purified further. Yield of 41: 1.65 g (98%). $^1$H NMR (400 MHz, $CDCl_3$) δ 2.63 (bs, 6H), 2.94 (m, 1H), 3.55 (m, 1H), 4.65 (m, 1H), 4.69 (m, 1H), 5.18 (m, 1H), 6.80 (d, J=5.4 Hz, 1H), 6.97 (d, J=7.6 Hz, 1H), 7.13 (t, J=8.4 Hz, 2H), 7.61 (m, 2H), 7.69 (s, 1H), 8.29 (d, J=5.4 Hz, 1H), 9.56 (d, J=7.6 Hz, 1H). MS (ESI+) 410.2 (under MS conditions, the aminal bond is cleaved and instead an M+1 peak is observed for the resulting 7-C(OH)HCH$_2$N(Me)H product).

Step 3: {2-(4-Fluorophenyl)-3-[2-(methylthio)pyrimidin-4-yl]imidazo[1,2-a]pyridin-7-yl}-2-(dimethylamino)ethanol (42)

A 100 mL round bottom flask was charged with oxazolidine 41 (1.65 g, 3.91 mmol), ethanol (50 mL), and sodium borohydride (450 mg, 11.9 mmol), and stirred at room temperature for 3 hours. The reaction was then quenched with 16 mL of a 20% $NH_4Cl$ aqueous solution and concentrated under reduced pressure, then diluted with water and neutralized with an aqueous solution of potassium carbonate. The solution was then extracted with methylene chloride (3×50 mL). The organic extracts were then pooled, dried over $MgSO_4$, filtered and concentrated under reduced pressure to give (dimethylamino)ethanol 42 (crude yield: 1.31 g, 78%). The crude product was then dissolved in a minimum volume of $CH_2Cl_2$, then loaded onto a 40 g Isco RediSep normal phase silica cartridge, and purified on an Isco OptiX10 CombiFlash instrument using a gradient that started at 100% methylene chloride and ended at 90% methylene chloride, 9% methanol, 1% concentrated ammonium hydroxide. Fractions containing desired product were pooled and concentrated under reduced pressure. Yield of 42: 1.01 g (60% over two steps). $^1$H NMR (400 MHz, DMSO-d6) δ 2.21 (s, 6H), 2.49 (m, 2H), 2.58 (s, 3H), 4.77 (m, 1H), 5.40 (bs, 1H), 6.86 (d, J=5.6 Hz, 1H), 7.16 (dd, J=7.2, 1.6 Hz, 1H), 7.29 (t, J=8.8 Hz, 2H), 7.64 (m, 3H), 8.45 (d, J=5.6 Hz, 1H), 9.32 (d, J=7.2 Hz, 1H). MS (ESI+) 424.2.

Step 4: 2-(4-Fluorophenyl)-3-[2-(methylsulfonyl)pyrimidin-4-yl]imidazo[1,2-a]pyridin-7-yl-2-(dimethylamino)ethanol (43)

A 100 mL round bottom flask containing sulfide 42 (720 mg, 1.70 mmol) was charged with methanol (20 mL), then a solution of Oxone (3.14 g, 5.10 mmol) in water (20 mL), then acetone (20 mL). After stirring at room temperature for 12 hours, the reaction was cooled to below −20° C. in a dry ice/isopropanol bath, then $SO_2$ was bubbled in for 5 minutes. The reaction was then concentrated under reduced pressure to remove organic solvent, and the resulting aqueous mixture was neutralized with an aqueous potassium carbonate solution. The resulting aqueous solution was extracted exhaustively into ethyl acetate, and the organic fractions were pooled, dried over $MgSO_4$, filtered, and concentrated under reduced pressure, and the sulfone product was not purified further. Yield of 43: 470 mg (61%). $^1$H NMR (400 MHz, DMSO-d6) δ 2.30 (s, 6H), 2.49 (m, 2H), 3.47 (s, 3H), 4.85 (m, 1H), 5.60 (m, 1H), 7.25 (d, J=7.4 Hz, 1H), 7.33 (t, J=8.8 Hz, 2H), 7.37 (d, J=5.6 Hz, 1H), 7.71 (m, 3H), 8.80 (d, J=5.6 Hz, 1H), 9.51 (d, J=7.4 Hz, 1H). MS (ESI+) 456.2.

Step 5: 1-[3-(2-Aminopyrimidin-4-yl)-2-(4-fluorophenyl)imidazo[1,2-a]pyridin-7-yl]-2-(dimethylamino)ethanol (44)

A pressure bottle containing sulfone 43 (320 mg, 0.703 mmol) was charged with tetrahydrofuran (40 mL), then chilled to <−40° C. in a dry ice/isopropanol bath. Ammonia gas (5.3 g, 0.31 mol) was then bubbled into the reaction. The pressure bottle was then sealed, and the reaction was allowed to warm to room temperature while stirring for 12 hours. The pressure was then released, and the reaction was concentrated under reduced pressure, dissolved in a minimum volume of $CH_2Cl_2$, then loaded onto a 40 g Isco RediSep normal phase silica cartridge, and purified on an Isco OptiX10 CombiFlash instrument using a gradient that started at 100% methylene chloride and ended at 90% methylene chloride, 9% methanol, 1% concentrated ammonium hydroxide. Fractions containing desired product were pooled and concentrated under reduced pressure. Yield of 44: 158 mg (57%). $^1$H NMR (400 MHz, DMSO-d6) δ 2.21 (s, 6H), 2.49 (m, 2H), 4.77 (m, 1H), 5.38 (m, 1H), 6.31 (d, J=5.4 Hz, 1H), 6.83 (bs, 2H), 7.04 (dd, J=7.2, 1.6 Hz, 1H), 7.28 (t, J=8.8 Hz, 2H), 7.60 (s, 1), 7.65 (m, 2H), 8.10 (d, J=5.4 Hz, 1H), 9.48 (d, J=7.2 Hz, 1H). MS (ESI+) 393.2.

EXAMPLE 8

4[2-(4-fluorophenyl)-7-(1-methyl-1-oxidopiperidin-4-yl)imidazo[1,2-a]pyridin-3-yl]pyrimidin-2-amine (45)

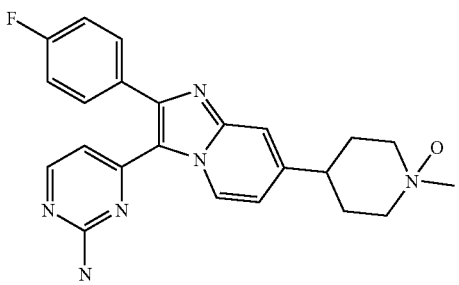

The N-oxide exemplified above can be prepared by treating a solution of 4[2-(4-fluorophenyl)l-7-(1-methylpiperidin-4-yl)imidazo[1,2-a]pyridin-3-yl]pyrimidin-2-amine(39) in anhydrous dichloromethane under nitrogen at 0° C. with one equivalent of 3-chloroperoxybenzoic acid. The resulting solution is allowed to stir for 15 minutes at 0° C., evaporated and purified as shown in the previous examples to yield N-oxide 45.

The following compounds can be prepared by a procedure similar to that exemplified in Example 8.

EXAMPLE 9

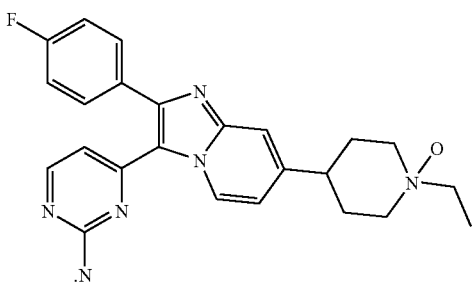

EXAMPLE 10

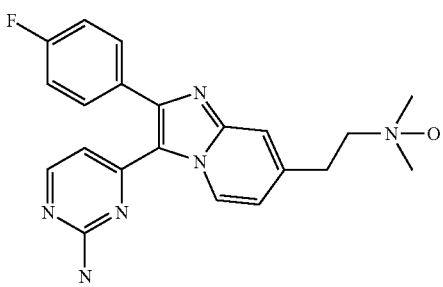

EXAMPLE 11

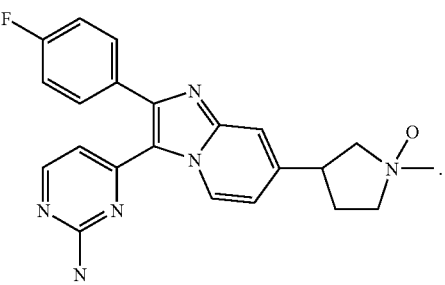

What is claimed is:

1. A compound having the formula (I):

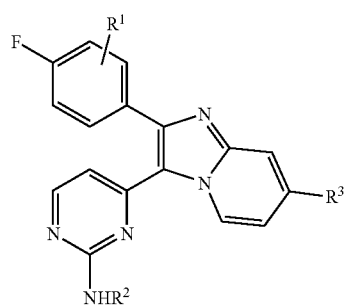

(I)

or a pharmaceutically acceptable salt, or an N-oxide thereof, wherein $R^1$ is hydrogen, methyl or fluoro;
$R^2$ is hydrogen or methyl;
$R^3$ is selected from -L-$NR^cR^d$, —$C(OH)R^b$—$CH_2$—$NR^cR^d$, [N—($C_{1-4}$) alkyl]piperidinyl, piperidin-4-yl, [N—($C_{1-4}$) alkyl]piperidin-4-yl, [N-methyl]piperidin-4-yl, [N-ethyl]piperidin-4-yl,

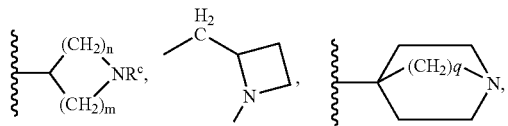

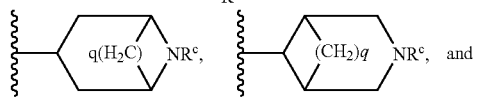

L is selected from —$(CR^aR^b)_{2-5}$— and

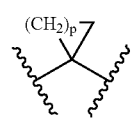

wherein one —(CR$^a$R$^b$) represents a 1,1-(C$_{3-6}$ cycloalkyl),
R$^a$ and R$^b$ are independently selected from hydrogen, OH, F, and C$_{1-4}$alkyl,
provided that when R$^a$ is OH, the R$^b$ attached to the C is hydrogen or C$_{1-4}$alkyl;
or R$^a$ and R$^b$, together with the C to which they are attached, form a C$_{3-6}$cycloalkyl;
R$^c$ and R$^d$ are independently selected from hydrogen and C$_{1-4}$alkyl;
n and m are independently 0, 1, 2, 3 or 4, provided that n+m=2, 3, or 4;
q is 1 or 2; and
p is 1,2 or 3.

2. The compound according to claim 1, or a pharmaceutically acceptable salt, or an N-oxide thereof, wherein

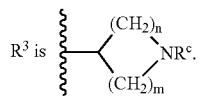

3. The compound according to claim 1, or a pharmaceutically acceptable salt, or an N-oxide thereof, wherein

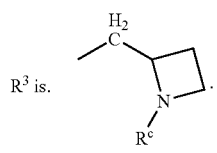

4. The compound according to claim 1, or a pharmaceutically acceptable salt, or an N-oxide thereof, wherein

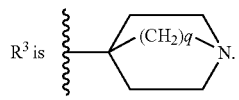

5. The compound according to claim 1, or a pharmaceutically acceptable salt, or an N-oxide thereof, wherein

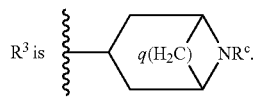

6. The compound according to claim 1, or a pharmaceutically acceptable salt, or an N-oxide thereof, wherein

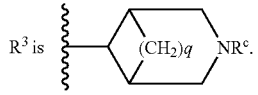

7. The compound according to claim 1, or a pharmaceutically acceptable salt, or an N-oxide thereof, wherein

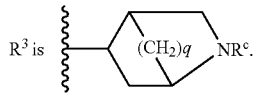

8. The compound according to claim 1, or a pharmaceutically acceptable salt, or an N-oxide thereof, wherein
R$^3$ is —C(OH)R$^b$—CH$_2$—NR$^c$R$^d$.

9. The compound according to claim 1, or a pharmaceutically acceptable salt, or an N-oxide thereof, wherein
R$^3$ is [N—(C$_{1-4}$)alkyl]piperidinyl.

10. The compound according to claim 1, or a pharmaceutically acceptable salt, or an N-oxide thereof, wherein
R$^3$ is piperidin-4-yl.

11. The compound according to claim 1, or a pharmaceutically acceptable salt, or an N-oxide thereof, wherein
R$^3$ is [N—(C$_{1-4}$) alkyl]piperidin-4-yl.

12. The compound according to claim 1, or a pharmaceutically acceptable salt, or an N-oxide thereof, wherein
R$^3$ is [N-methyl]piperidin-4-yl.

13. The compound according to claim 1, or a pharmaceutically acceptable salt, or an N-oxide thereof, wherein
R$^3$ is [N-ethyl]piperidin-4-yl.

14. The compound according to claim 1, or a pharmaceutically acceptable salt, or an N-oxide thereof, wherein

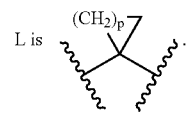

15. The compound according to claim 1, or a pharmaceutically acceptable salt, or an N-oxide thereof, wherein
L is —(CR$^a$R$^b$)$_{2-5}$—, and one —(CR$^a$R$^b$) represents a 1,1-(C$_{3-6}$cycloalkyl).

* * * * *